United States Patent
Somma et al.

(10) Patent No.: US 9,156,034 B2
(45) Date of Patent: Oct. 13, 2015

(54) PROCESS FOR RECYCLING ABSORBENT SANITARY PRODUCTS

(71) Applicant: FATER S.p.A., Pescara (IT)

(72) Inventors: Marcello Somma, Pescara (IT); Giorgio Vaccaro, Pescara (IT); Jan K. Michalek, Pataskala, OH (US); Theodore Thomas, Columbus, OH (US)

(73) Assignee: FATER S.p.A., Pescara (IT)

( * ) Notice: Subject to any disclaimer, the term of this patent is extended or adjusted under 35 U.S.C. 154(b) by 155 days.

(21) Appl. No.: 13/686,842

(22) Filed: Nov. 27, 2012

(65) Prior Publication Data

US 2013/0153692 A1  Jun. 20, 2013

(30) Foreign Application Priority Data

Nov. 28, 2011 (IT) .............................. TO2011A1091

(51) Int. Cl.
| | |
|---|---|
| *A61L 2/08* | (2006.01) |
| *B02C 1/00* | (2006.01) |
| *B02B 5/02* | (2006.01) |
| *B02C 19/00* | (2006.01) |
| *A61L 2/07* | (2006.01) |

(Continued)

(52) U.S. Cl.
CPC . *B02C 19/00* (2013.01); *A61L 2/07* (2013.01); *A61L 11/00* (2013.01); *B09B 3/0083* (2013.01)

(58) Field of Classification Search
CPC ............... A61L 2/00; A61L 2/07; A61L 9/03; A61L 11/00; B09B 3/00; B09B 3/0075
USPC ......... 422/1, 26, 33, 295, 297, 300, 305, 307, 422/309; 261/83; 92/171.1; 241/15, 23, 241/24.19, 25

See application file for complete search history.

(56) References Cited

U.S. PATENT DOCUMENTS

| | | | |
|---|---|---|---|
| 4,059,919 | A | 11/1977 | Green |
| 4,303,501 | A | 12/1981 | Steffens |

(Continued)

FOREIGN PATENT DOCUMENTS

| | | |
|---|---|---|
| DE | 2826880 A1 | 1/1979 |
| DE | 9000869 U1 | 3/1990 |

(Continued)

OTHER PUBLICATIONS

Italian search report for application No. TO20111091 dated Mar. 28, 2012.

(Continued)

*Primary Examiner* — Monzer R Chorbaji

(74) *Attorney, Agent, or Firm* — Patterson & Sheridan, L.L.P.

(57) ABSTRACT

A process for treating used absorbent sanitary products, comprising the steps of providing a rotary cylindrical autoclave having an inner surface and two ends, at least one of which terminates in a hatch that can be opened to enable access to said autoclave and sealably closed to enable pressurization of said autoclave; loading said autoclave with closed absorbent sanitary products; heating and pressurizing the autoclave to a sterilization temperature and at the same time driving the autoclave in rotation about a longitudinal axis thereof, wherein said step of heating and pressurizing the autoclave envisages a first temperature regime for the products contained in the autoclave and a second temperature regime, higher than the first temperature regime, for said inner surface.

4 Claims, 2 Drawing Sheets

(51) Int. Cl.
*A61L 11/00* (2006.01)
*B09B 3/00* (2006.01)

(56) References Cited

U.S. PATENT DOCUMENTS

| | | | |
|---|---|---|---|
| 4,970,267 A | 11/1990 | Bailey et al. | |
| 5,292,075 A | 3/1994 | Bartlett | |
| 5,361,994 A | 11/1994 | Holloway | |
| 5,429,311 A | 7/1995 | Cina et al. | |
| 5,558,745 A | 9/1996 | Conway et al. | |
| 5,618,003 A | 4/1997 | Akiyoshi et al. | |
| 5,799,883 A | 9/1998 | Lewis et al. | |
| 6,200,715 B1 | 3/2001 | Fuller et al. | |
| 6,238,516 B1 | 5/2001 | Watson et al. | |
| 7,407,912 B2 | 8/2008 | Mertens et al. | |
| 2003/0129915 A1 | 7/2003 | Harriz | |
| 2005/0155491 A1 | 7/2005 | Faust et al. | |
| 2007/0135563 A1 | 6/2007 | Simmons et al. | |
| 2007/0142532 A1 | 6/2007 | Lee | |
| 2009/0032626 A1 | 2/2009 | Armstrong et al. | |
| 2010/0093949 A1 | 4/2010 | Herfert et al. | |
| 2010/0292401 A1 | 11/2010 | Grimes | |

FOREIGN PATENT DOCUMENTS

| | | | |
|---|---|---|---|
| DE | 4133699 A1 | 4/1993 | |
| DE | 19631442 A1 | 2/1998 | |
| DE | 19749039 A1 | 7/1999 | |
| DE | 19821473 A1 | 11/1999 | |
| EP | 0739657 A1 | 10/1996 | |
| EP | 0983803 A1 | 3/2000 | |
| EP | 2098308 A2 | 9/2009 | |
| GB | WO 2006056768 | * 6/2006 | ......... B01J 3/04 |
| JP | 2004113915 A | 4/2004 | |
| JP | 4056839 B2 | 3/2008 | |
| JP | 4685973 B1 | 5/2011 | |
| WO | 9207995 A1 | 5/1992 | |
| WO | 9420668 A1 | 9/1994 | |
| WO | 9524967 A1 | 9/1995 | |
| WO | 9627045 A1 | 9/1996 | |
| WO | 03039731 A1 | 5/2003 | |
| WO | 2006056768 A2 | 6/2006 | |
| WO | 2006079842 A1 | 8/2006 | |
| WO | 2010065088 A1 | 6/2010 | |

OTHER PUBLICATIONS

Zohuriaan-Mehr et al., Superabsorbent Polymer Materials: A Review, Iranian Polymer Journal, 2008, 17(6), pp. 451-477.

* cited by examiner

PROCESS FOR RECYCLING ABSORBENT SANITARY PRODUCTS

CROSS-REFERENCE TO RELATED APPLICATIONS

This application claims benefit of Italian Patent Application Application No. TO2011A001091, filed Nov. 28, 2011, which is herein incorporated by reference.

BACKGROUND OF THE INVENTION

1. Field of the Invention

The present invention relates to a process for recycling used absorbent sanitary products.

By the term "absorbent sanitary products" is meant in general disposable absorbent products, such as: baby diapers, incontinence absorbent pads, ladies sanitary pads, bed mats, etc.

2. Description of the Related Art

Absorbent sanitary products are generally made up of a wide range of different materials, amongst which sheets of plastic material, cellulose fluff, superabsorbent polymers, sheets of non-woven fabric, etc.

Absorbent sanitary products contain high-quality materials such as plastic and cellulose, and it would be desirable to recover said materials to use them in a new production cycle or else for the production of energy.

Currently, used absorbent sanitary products are disposed of as undifferentiated waste to be sent to rubbish dumps. The component materials of used absorbent sanitary products are not recovered in the first place because the various materials (cellulose fibres, superabsorbent polymers, sheets of plastic material, etc.) are intimately interconnected, and to obtain separation of the materials it would be necessary to carry out a complete destructuring of the products. In addition, used absorbent sanitary products contain organic excretions and bacteria, and it would be necessary to carry out a sterilization of the products prior to recycling of the materials.

For the above reasons, used absorbent sanitary products are not included amongst recyclable waste products for which differentiated collection is carried out.

It is estimated that absorbent sanitary products constitute approximately 2-3% of the total of urban solid waste. However, where a differentiated collection is carried out with a high percentage of differentiation of the waste (with a percentage of differentiated waste higher than 60% of the total) the percentage of absorbent sanitary products with respect to the remaining part constituted by the undifferentiated residual fraction rises to approximately 20%.

The high percentage of absorbent sanitary products with respect to the residual fraction of non-recyclable waste renders highly desirable the availability of equipment and processes that enable a treatment of absorbent sanitary products to be carried out aimed at recycling their component materials in an efficient and economically convenient way.

Currently known techniques for treatment of used absorbent sanitary products are not satisfactory. A first known technique envisages carrying out washing of the used absorbent products with water, alkalis, and soap and separating the cellulose from the plastic during the washing operation. Examples of this technique are disclosed in the documents Nos. WO 94/20668 and WO 96/27045.

The document No. U.S. Pat. No. 5,292,075 describes a process in which the dirty absorbent sanitary products are preliminarily shredded. The shredded material is then washed in a washing machine comprising a perforated cylindrical drum that withholds the plastic material inside it. The material containing the cellulose pulp is then dehydrated.

These techniques of treatment of absorbent sanitary products are in actual practice problematical to implement since the washing water would contain a high amount of pollutants, such as gelified superabsorbent polymers and organic residue, which renders problematical disposal thereof. Drying of the cellulose after washing moreover entails a high expenditure of energy.

A further difficulty derives from the fact that used absorbent sanitary products are normally thrown away in folded and closed to form a pack, with the outer plastic layer of the products that forms an impermeable barrier. If the products are treated in the form in which they have been thrown away, the outer impermeable layer prevents an effective sterilization of the products. On the other hand, a preliminary treatment as described in U.S. Pat. No. 5,292,075 entails the need to shred articles with a high content of organic excretions, bacteria, and contaminants.

The document No. JP 2004113915 describes a process for treating diapers that contain absorbent polymers, whereby the used diapers are set in a pressurized closed vessel together with sawdust. Inside the vessel the diapers are treated with steam at high temperature and high pressure for a pre-set time. Steam treatment is carried out at a pressure of 15-25 atm and at a temperature of 150-250° C. This document envisages use of the absorbent sanitary products, after said treatment, as fertilizers following upon fermentation.

The document No. WO 2010/065088 describes an autoclave for the treatment of urban solid waste that envisages drying of the waste using steam. The apparatus described in the document WO 2010/065088 comprises a rotary cylindrical autoclave provided with at least one hatch that can be opened to enable access to the autoclave and sealably closed to enable pressurization of the autoclave, an inlet for contact steam that comes into direct contact with the waste contained inside the autoclave, a plurality of straight hollow blades, which are designed to conduct non-contact steam, project from the inner surface of the autoclave, and are supplied with non-contact steam. This apparatus enables sterilization of urban solid waste and drying of the waste during treatment in the autoclave. The apparatus described in the document WO 2010/065088 has been developed for treatment of undifferentiated urban solid waste and does not contains specific teachings to obtain sterilization, drying, and separation of the component materials of absorbent sanitary products.

SUMMARY OF THE INVENTION

The object of the present invention is to provide a process for treating used absorbent sanitary products that will enable sterilization, drying, and destructuring of used absorbent sanitary products in order to carry out recovery of the constituent materials.

According to the present invention, the above object is achieved by a process having the characteristics forming the subject of Claim 1.

The claims form an integral part of the teaching provided herein in relation to the invention.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
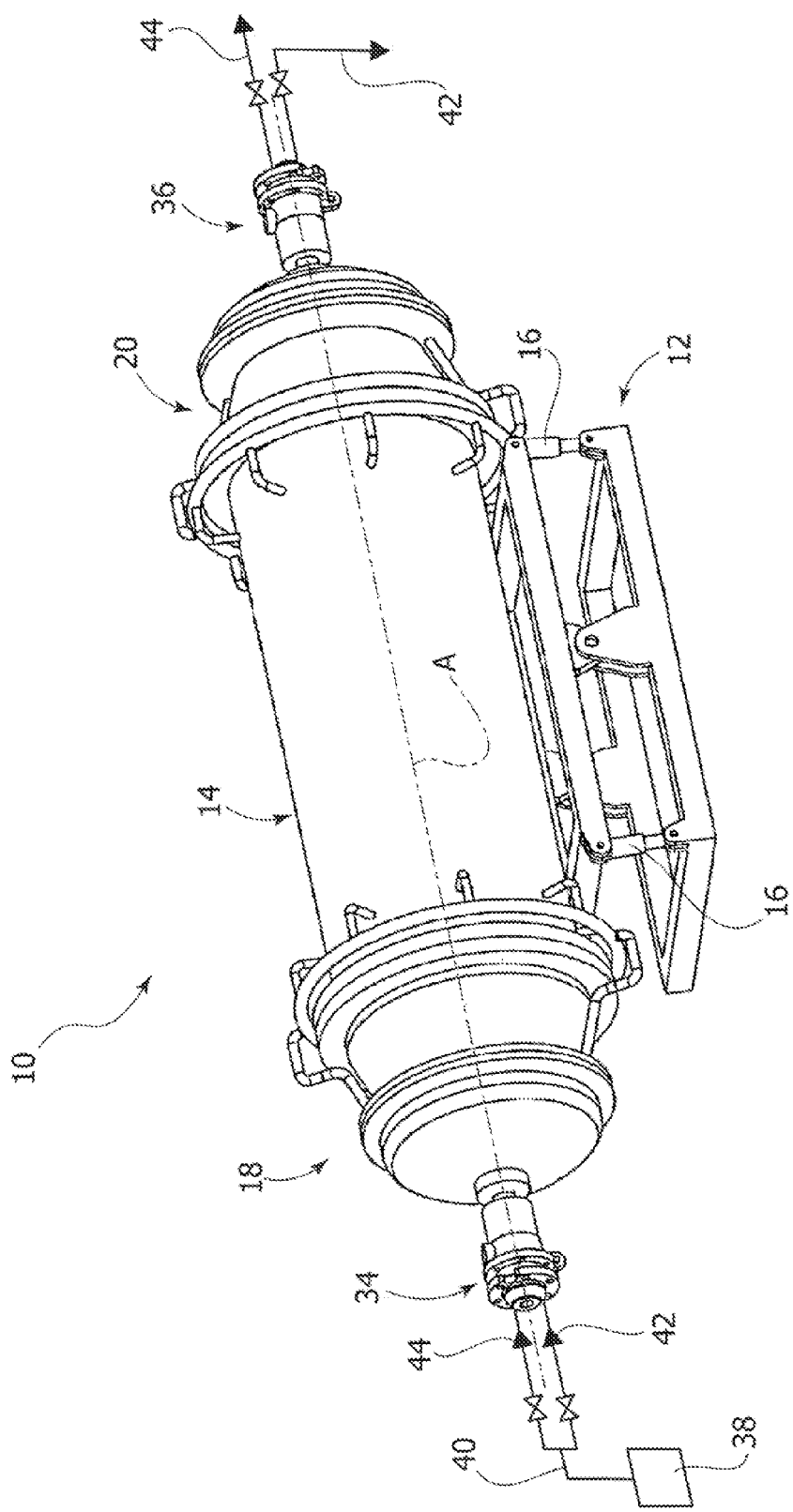
FIG. 1 is a perspective view of a rotary-autoclave apparatus for treating waste.

With reference to FIG. 1, designated by 10 is a rotary-autoclave apparatus for treating used absorbent sanitary products. The apparatus 10 comprises a stationary structure 12, which carries a cylindrical autoclave 14 that turns about its longitudinal axis A. The apparatus 10 comprises a driving device (not illustrated), which drives the autoclave 14 in rotation about the axis A. The supporting structure 12 may be provided with actuators 16 for varying the inclination of the autoclave 14 with respect to a horizontal axis, which enables tilting of the autoclave 14 between a loading/unloading position and a working position. The autoclave 14 has two ends, at least one of which terminates in a hatch that can be opened to enable access to the internal space of the autoclave and sealably closed to enable pressurization of the internal space. In the example illustrated two openable hatches 18, 20 are provided, which can be used, for example, for loading the autoclave with the products to be treated and for unloading the treated products. Alternatively, a single openable hatch could be provided, which can be used both for loading and for unloading.

The apparatus 10 comprises a circuit for heating and pressurizing the autoclave 14 in order to heat the absorbent sanitary products to a sterilization temperature.

Figure 2:
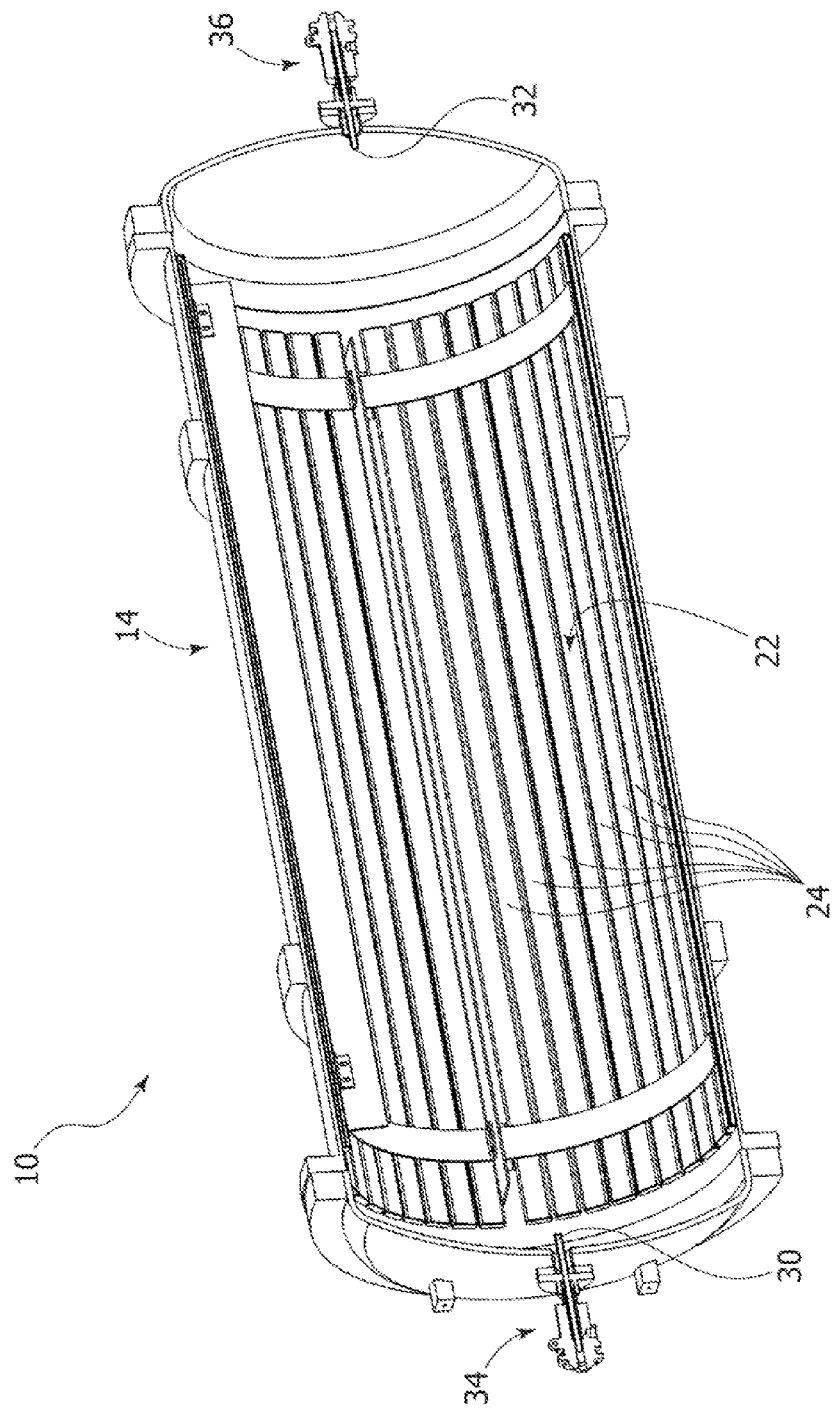
FIG. 2 is a sectional perspective view of the autoclave of FIG. 1.

FIG. 2 is a schematic sectioned view of the autoclave 14. In FIG. 2 it may be noted that the autoclave 14 has an inner surface 22 that delimits a treatment volume. Arranged within the autoclave 14 is a plurality of ducts 24 that form a part of the inner surface 22. The ducts 24 extend parallel to the longitudinal axis A and are connected at their opposite ends to respective headers for inlet and outlet of heating steam. The steam that traverses the ducts 24 does not come into contact with the products to be treated contained in the internal volume of the autoclave 14 and is consequently referred to as "non-contact steam".

The hatches 18, 20 are provided with respective rotary connectors 34, 36 for inlet and outlet of heating steam coming from a steam generator 38. The flow of heating steam can be divided into a flow of non-contact steam 42 that traverses ducts located on the inner wall of the autoclave 14 and a flow of contact steam 44 that comes into direct contact with the products to be treated and pressurizes the internal volume of the autoclave 14. On the outlet connector 36 the flow of non-contact steam 42 and the flow of contact steam 44 are divided and treated separately, for example as described in the document No. WO 2010/065088.

Typically, absorbent sanitary products comprise an absorbent core of cellulose fibres and of superabsorbent polymers. The absorbent core is usually enclosed between two sheets of plastic material joined together. Typically, the backsheet is impermeable, whereas the topsheet is porous. Used absorbent sanitary products are normally folded up so as to enclose the product in the form of a pack within the impermeable backsheet. Usually adhesive tabs are provided for closing the folded product. The organic excretions are thus enclosed within a sealed sheet of impermeable plastic material.

The present invention envisages carrying out the treatment of absorbent sanitary products just as they are collected, i.e., in the form where they are closed to form a pack, and without any preliminary treatment for opening the products.

To obtain an effective action of drying and sterilization during treatment in the autoclave 14, it is necessary to obtain destructuring of the products so as to expose all the organic substances to the sterilization temperature in every point inside the autoclave 14. Destructuring of the absorbent sanitary products is absolutely essential to obtain a complete sterilization and to separate the plastic and the cellulose fibres from one another.

In operation, the autoclave 14 is loaded with a load of absorbent sanitary products. The autoclave 14 is then sealably closed and pressurized by the contact steam. At the same time, the autoclave is heated by the non-contact steam inside the ducts 24. The autoclave, once heated and pressurized, is driven in rotation about the axis A.

It has been found that low operating temperatures of the autoclave 14 are insufficient to produce opening of the products, whereas excessively high temperatures cause wrinkling of the topsheets of plastic material rendering separation problematical, which on the one hand jeopardizes the effectiveness of the sterilization process and on the other renders the material at output from the autoclave 14 unusable. It is only the use of intermediate temperatures that enables opening of the products but not destructuring thereof and that enables exposure of the cellulose fibres and the organic liquids absorbed thereby to the treatment.

More precisely, it has been found that the plastic backsheets of absorbent sanitary products undergo wrinkling at temperatures higher than 150° C., whereas a temperature of approximately 138° C. is sufficient for melting the glue that keeps the absorbent sanitary products joined together, enabling opening of the products and optimal exposure to the action of sterilization of the contact steam.

Moreover, temperatures higher than 140° C. enable destruction of plastic bags that may contain the absorbent sanitary products.

The present invention envisages carrying out the treatment of used absorbent sanitary products in an rotary steam autoclave that provides two or more simultaneous temperature regimes.

With a pressurized rotary autoclave with dual steam supply, the steam in direct contact with the waste can be introduced into and extracted from the autoclave so as to maintain a preferred temperature regime according to the contents. It has been found that this preferred temperature is in the range between 138 and 152° C. In fact, it has been found that at temperatures substantially higher than 150° C. the outer envelope of the absorbent sanitary products undergoes wrinkling, whereas a temperature of 138° C. is sufficient to cause yielding of the glue that holds together the absorbent sanitary products, enabling the products to open out and expose the inside of them to the action of the contact steam. This temperature range enables a complete sterilization of the bacterial charges present in the absorbent sanitary products. Moreover, temperatures higher than 138° C. enable the contact steam to destroy the bags in which the absorbent sanitary products may be contained.

The non-contact steam inside the ducts 24, isolated from the waste, is used for creating hot points on the walls of the autoclave, which damage and cause yielding of the plastic backsheets of the absorbent sanitary products protecting, however, the plastic sheets from wrinkling. Said hot points create points of localized melting that open up holes in the plastic sheets and weaken the outer envelopes in such a way that the action of agitation inside the rotary autoclave causes tearing of the outer envelopes, destructuring of the products, and complete exposure of the absorbent cores to the contact steam. When the plastic backsheets are damaged, the absorbent cores of cellulose fibres and superabsorbent polymers enclosed in the plastic backsheets separate easily from the plastic backsheets thanks to the action of shaking inside the autoclave. It has been found that the temperature of the wall of the autoclave 14 necessary to obtain said effects is comprised in the range between 160 and 200° C., and preferably between 165 and 175° C. A temperature of approximately 170° C. corresponds to the temperature of decomposition of the plastic material forming the topsheets of the absorbent sanitary products.

The dual temperature regime enables a complete destructuring of the absorbent sanitary products inside the autoclave 14. In this way, there is avoided the need for a preliminary treatment of shredding of the products, which would expose the operators and the surrounding environment to evil odours and to the contaminating elements contained in the absorbent sanitary products.

Complete destructuring of the products during treatment in the autoclave enables drying and sterilization of the products in shorter times. Given that the contents of the autoclave are damp, the immediate effect on the hot points of the wall is the creation of flashes of steam at the pressure existing in the autoclave. This difference in temperature enables a relatively high level of heat exchange. When the pressure of the steam exceeds the saturation temperature/pressure, the steam in excess is evacuated outwards, thus enabling drying also during the heating step. After treatment in the autoclave, a dried and sterile destructured mass is obtained basically formed by plastic and cellulose fibres. Next, the dried and sterile destructured mass is passed through a sieve in which the plastic and the cellulose fibres are separated.

While the foregoing is directed to embodiments of the present invention, other and further embodiments of the invention may be devised without departing from the basic scope thereof, and the scope thereof is determined by the claims that follow.

The invention claimed is:

1. A process for treating used absorbent sanitary products, comprising the steps of:
    providing a rotary cylindrical autoclave having an inner surface and two ends, at least one of which terminates in a hatch that can be opened to enable access to said autoclave and sealably closed to enable pressurization of said autoclave;
    loading said autoclave with closed absorbent sanitary products;
    heating and pressurizing the autoclave to a sterilization temperature and at the same time driving the autoclave in rotation about a longitudinal axis thereof,
    wherein said step of heating and pressurizing the autoclave envisages a first temperature regime for the products contained in the autoclave and a second temperature regime, higher than the first temperature regime, for said inner surface, and
    wherein the first temperature regime is provided by contact steam in direct contact with the products contained in the autoclave and said second temperature regime is provided by non-contact steam that traverses ducts located on the inner surface of the autoclave.

2. The process according to claim 1, wherein said first temperature regime is comprised between 138 and 152° C.

3. The process according to claim 1, wherein said second temperature regime is comprised between 160 and 200° C.

4. The process according to claim 1, wherein said second temperature regime is comprised between 165 and 175° C.

* * * * *